United States Patent [19]

Moore

[11] Plant 5,032

[45] Apr. 12, 1983

[54] ROSE PLANT

[76] Inventor: Ralph S. Moore, 2519 E. Noble Ave., Visalia, Calif. 93277

[21] Appl. No.: 308,488

[22] Filed: Oct. 5, 1981

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

This invention relates to a new and distinct variety of miniature rose plant primarily identified by its very double pink flower and the abundance of bloom.

1 Drawing Figure

The present invention relates to a new and distinct variety of hardy, dwarf, bush type rose plant of the miniature class; the variety being primarily characterized—as to novelty—by the soft to medium pink very double flowers.

The variety is further characterized by:

An abundance of bloom, with flowers usually borne singly, but also several to the stem in loose clusters.

Little or no fragrance.

A plant which is vigorous, of rounded, compact habit with small matte foliage with pointed leaflets; the buds and flowers being similar in form and size to June Time (miniature—U.S. Plant Pat. No. 2,563).

The plant, which has a normal height of about 8 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Fairy Moss (U.S. Plant Pat. No. 3,083—miniature) as the seed parent and Fairy Moss (miniature) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers (photo was made of flowers grown in plastic greenhouse).

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety identification.*—MORfair (Commercial synonym: Pink Cherub).

Flowers borne: Singly and several together on short slender stems.

Quantity of bloom: Abundant both outside and in greenhouse.

Bud:

*Peduncle.*—Medium length; slender but sturdy; erect; medium to light green, with few or no prickles and few or no short hairs.

*Before calyx breaks.*—Size — small. Form medium long; pointed with several foliaceous appendages and occasional hairs on surface of bud; with foliaceous parts extending beyond the tip of the bud equal to about one-half of its length.

*Color.*—Medium green.

*As calyx breaks.*—Color — pink.

*Opening.*—Opens well in all weather.

Bloom:

*Size when fully open.*—Small, averaging about 30 mm (1¼").

*Petalage.*—Double to very double — averaging about 50–60 petals, arranged regularly plus several small petaloids.

*Form.*—Cupped or flat at first becoming more high centered with petals rolled loosely outward and downward. Open flowers usually do not show stamens.

Petals: Fairly thick; satiny on inside and on outside surface.

*Shape.*—Outside petals, broad lanceolate (nearly round) with small acute tip; intermediate — broad lanceolate with rounded tip (sometimes with very short acute tip); inside — lanceolate with very short acute tip.

Color: Newly opened flower from a plant grown in plastic greenhouse (September 1981), Visalia, Calif.:

*Outside petal.*—Outside surface — near Phlox Pink 625/3 or lighter with small soft yellowish area at base. Inside surface — near Phlox Pink 625/3 with small soft yellowish area at base.

*Intermediate petal.*—Outside surface — near Phlox Pink 625/2 with lighter area at base. Inside surface — near Phlox Pink 625/2 with small light yellow area at base.

*Inner petal.*—Outside surface — similar to intermediate petal, with small yellow area at base. Inside surface — similar to intermediate petal (may be slightly darker pink at times).

*General color effect.*—Newly opened flowers — pink; flowers often appear darker pink in center shading to lighter pink on outer (older) portion.

*Three days open.*—Color — pink with center portion becoming lighter pink (more nearly color of outer petals).

*Behavior.*—Opens well in all weather. Spent petals drop off.

*Flower longevity* (*August* 1981).—Plant in pot 4–6 days or longer. Cut flowers at living room temperature 3–4 days or longer.

Reproductive organs:

*Stamens.*—Usually few or none.

*Filaments.*—Varying length, if present.

*Anthers.*—Few or none.

*Pollen.*—Usually none.

*Pistils.*—Average number — very small.

*Styles.*—Varying length; pale yellowish; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; small; leathery; matte.

*Leaflets.*—Shape: broad, nearly oval; apex acute; base acute (sometimes rounded). Color: medium green; new growth — normal (medium) green.

*Rachis.*—Medium strength; upper side usually smooth with few or no tiny prickles or hairs; grooved; underside may have few to several tiny short prickles.

*Stipules.*—Medium to long; medium to narrow width; medium to short length narrow points which turn out usually at about 45 degrees or more.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Few to average.

*Prickles.*—None.

*Hairs.*—None.

*Branches.*—Color: medium green. Thorns: several; slender; brownish. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy; dwarf, bushy, rounded, much branched habit, substantially as illustrated and described, characterized by buds and flowers that are essentially pink in color, the outer petals being generally of a lighter pink than the inner petals giving the freshly open flower a blended or two color effect; the general habit of growth as well as flower form and color being similar to June Time (miniature—U.S. Plant Pat. No. 2,563), and further characterized by a plant of compact well rounded shape; vigorous; the said plant being easy to propagate from cuttings, with an abundance of small matte foliage and an abundance of flowers borne singly or several to the stem in loose clusters.

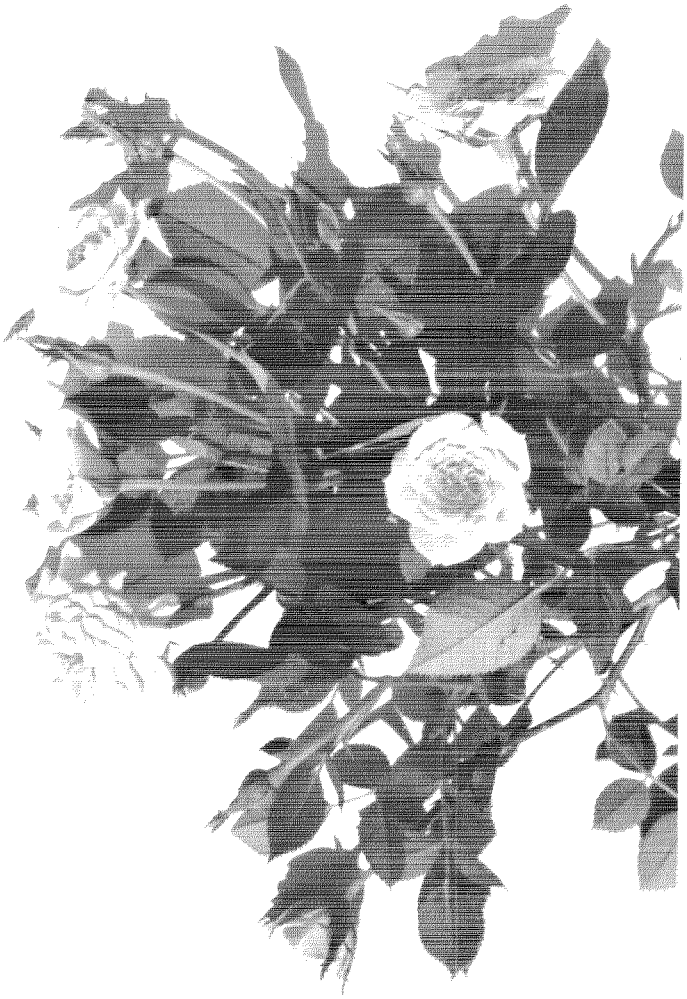

* * * * *